United States Patent [19]
Abrutyn et al.

[11] Patent Number: 4,859,446
[45] Date of Patent: Aug. 22, 1989

[54] PROCESS FOR PREPARING BASIC ALUMINUM COMPOUNDS HAVING INCREASED SWEAT RESISTANT ACTIVITY

[75] Inventors: Eric S. Abrutyn, Middletown; Robert J. Sloan, Port Jervis, both of N.Y.

[73] Assignee: Wickhen Products, Inc., Huguenot, N.Y.

[21] Appl. No.: 943,443

[22] Filed: Dec. 18, 1986

[51] Int. Cl.$^4$ .................. A61K 7/32; A61K 7/38; A61K 9/12; C01B 7/00
[52] U.S. Cl. .................. 423/462; 423/467; 424/DIG. 5; 424/47
[58] Field of Search .................. 424/68; 423/462

[56] References Cited

U.S. PATENT DOCUMENTS 3,873,686 3/1975 Beekman .................. 424/68
4,359,456 11/1982 Gosling et al. .................. 424/68

Primary Examiner—Dale R. Ore
Attorney, Agent, or Firm—Steele, Gould & Fried

[57] ABSTRACT

An improved process for preparing an enhanced antiperspirant active polymeric aluminum compound having the empirical formula:

$$Al_2(OH)_{6-a}X_a \qquad (I)$$

wherein X is Cl, Br, F, I, SO$_4$ and NO$_2$, a is about 1.0 to about 4, which is further characterized by (a) a Size Exclusion Chromatograph, (b) a Band III percent aluminum value of at least 40 percent, and preferably (c) a Band I percent aluminum value of not greater than 5 percent, and compositions thereof.

10 Claims, No Drawings

PROCESS FOR PREPARING BASIC ALUMINUM COMPOUNDS HAVING INCREASED SWEAT RESISTANT ACTIVITY

BACKGROUND OF THE INVENTION

1. Field of the Invention

The present invention relates to a novel process for preparing basic aluminum compounds having a high yield of a polymeric species with increased reduced sweat activity. More particularly, the present process prepares a single species of the basic aluminum compounds with the exclusion of the less active higher molecular weight basic aluminum compounds.

2. Prior Art

Basic aluminum compounds, particularly, basic aluminum halides, have long been used as antiperspirants. Generally, such basic aluminum compounds are, in the presence of water, complexes made up of mixtures of polymeric species of various sizes and molecular structures. It is known that basic polymeric aluminum species exist which have increased antiperspirant activity. These increased active basic polymeric aluminum compounds have an aluminum to anion molar ratio of from 0.5 to 2.5:1 and are determinable by several different standard tests, for example, the Size Exclusion Chromatographic Test. These aluminum compounds have been called Band III Aluminum Compounds.

U.S. Pat. No. 3,873,686 to S. M. Beekman discloses the general practice of preparing aluminum chlorhydroxide $Al_2(OH)_5Cl$ by the procedure of reacting 5 atomic weights of aluminum with 1 mole of aluminum chloride in an aqueous solution at 80° to 90° C. followed by filtration to remove trace insolubles and then spray dried.

U.S. Pat. No. 4,359,456 to Gosling et al, which is incorporated herein by reference, discloses a process for preparing an increased active antiperspirant polymeric aluminum hydroxy halide by a conventional step of prolonged heating of an aqueous solution containing a basic aluminum compound having substantially the same empirical formula as the polymeric aluminum compound prepared. Low concentration of starting material and elevated temperature aging have been stated as being critical in obtaining good yields of the enhanced active aluminum compound. However, the other species of basic aluminum halides having lesser antiperspirant activity are still present.

German application P 2900711.0 describes basic aluminum chloride, bromide, iodide and nitrate compounds having enhanced antiperspirant activity which is obtained by the conventional step of heating aqueous solutions of the components under conditions leading to formation of a greater proportion of the lower molecular weight polymeric species having a size about 100 Angstroms together with the higher molecular weight species.

U.K. Patent Application GB 2048229A discloses an aluminum chlorhydroxide which comprises at least 45% by weight of an aluminum group of aluminum chlorhydroxide complexes which is characterized by exhibiting anomalous permeation and reaction rates in the gel permeation chromatography and ferron tests. The aluminum chlorhydroxide is prepared by the elevated temperature aging of aluminum chlorhydroxide in an aqueous medium.

European Patent Application 6739 discloses a process for preparing a greater percentage of enhanced antiperspirant active species of polymeric basic aluminum halides which have been referred to as Band III aluminum compounds that is found in combination with the Band I and Band II species. The process involves a conventional heating step and aging at elevated temperatures.

It is recognized that in the preparation of the polymeric aluminum compounds, there are many factors which must be considered in order to obtain a higher ratio of the desired Band III aluminum compounds. The starting materials, their concentration, the temperatures utilized in the process and the time of aging are all critical in avoiding a polymeric shift to one of the lesser desirable basic aluminum compounds. Since lower concentrations of starting materials has been considered as being critical for obtaining a higher ratio of the desired enhanced active compounds, low yields are expected to result in their production, but still the other species of the polymeric aluminum compounds are expected to be present.

Conventional aluminum chlorohydrate for example, WICKENOL 323, which is marketed by Wickhen Products, Inc., primarily consists of complex polymeric species which generally used for purposes of the invention are depicted as having the empirical formula: $Al_2(OH)_{6-a}X_a$, wherein a is about 1.0 to 4.

In the Size Exclusion Chromatography Test which is referred herein, there are three major bands detected in conventional aluminum chlorohydrate compounds. The Band I species is the largest of the group having antiperspirant activity. The species which possesses increased sweat resistance is known as the Band III aluminum compound. This species has a lower molecular weight and shows only a small size band.

It should be understood that the above formula is greatly simplified and is intended to include basic aluminum chlorides containing coordinated or bound molecules of water as well as basic aluminum chloride polymers, complexes and mixtures of the above.

Particularly suitable for the purposes of the present invention are basic aluminum chlorides having a basicity in the range of about two-thirds to five-sixths; that is compounds of the above general formula having a predominance of units of $Al_2(OH)_4Cl_2$ and/or $Al_2(OH)_5Cl$, such that the aluminum to chlorine mol ratio ranges from about 1.0 to 2.0.

Teagarden et al in the article entitled "Aluminum Chlorohydrate I: Structure Studies", Journal paper 8254, Purdue University Agricultural Experimental Station, West Lafayette, IN 47907 reports that X-ray diffraction and IR and Al-NMR spectroscopy indicates that aluminum chlorohydrate is composed of a central aluminum in a tetrahedral configuration surrounded by 12 aluminum atoms in octahedral configuration. The proposed structure of aluminum chlorohydrate is $Al_{13}O_4(OH)_{24}(H_2O)_{12}Cl_7$.

Teagarden et al in the article entitled "Aluminum Chlorohydrate II: Physiochemical Properties", Journal paper 8254, Purdue University Agricultural Experimental Station, West Lafayette, IN 47907, reports that based on the reaction rate with ferron, the distribution of aluminum species in aluminum chlorohydrate can be classified as 4% monomeric aluminum, 8% small polycation and 88% large polycation.

Because of the volume limitations in aerosols, merely increasing the amount of polymer aluminum chlorohydrate to increase the amount of the enhanced antiperspirant active species of the aluminum compound is not always feasible. Isolation or separation of the enhanced active species from the lesser active species for use to increase their amounts would increase costs. It is therefore highly desirable to provide a process for increasing the percentage of the enhanced active Band III species which is produced in a single step process. It is even more desirable to prepare only Band III aluminum compounds. It is further desirable to produce the enhanced active Band III species in a single process operation without isolation and/or elevated temperature aging starting with conventional aluminum chloride or aluminum metal.

SUMMARY OF THE INVENTION

The present invention relates to an improved process for preparing an enhanced antiperspirant active polymeric aluminum compounds having the empirical formula:

$$Al_2(OH)_{6-a}X_a \qquad (I)$$

wherein X is Cl, Br, I, SO$_4$ or NO$_2$, a is about 1.0 to about 4.0, which is further characterized by (a) a Size Exclusion Chromotagraphy Test Band having a relative retention time corresponding to Band III of the Standard Basic Aluminum Chloride Solution Size Exclusion Chromatogram, and (b) a Band III percent aluminum value of at least 40 percent, preferably 90 percent. Advantageously, the aluminum compound has at least a Band I percent aluminum value of not greater than 5%.

According to the invention a preferred process for making an aqueous solution of an enhanced active antiperspirant compound comprises reacting an aqueous solution of an aluminum compound of the empirical formula: $Al_nX_m$, wherein X is as hereinbefore described, n is 1 or 2, and m is 1 or 3, with aluminum metal at a temperature between 50° C. and 195° C., preferably about 100° to 120° C., until a ratio of aluminum to anion of 0.5–2.5:1, preferably 0.90–2.05:1, is obtained, and an amount of about 90–100% of the recovered product is Band III aluminum compound.

Alternately, the process of the invention can be practised by the preparation of the $Al_nX_m$ compound, preferably, aluminum metal with an inorganic acid, and then continuing the reaction by the controlled addition of aluminum until the desired ratio of aluminum to anion is obtained.

It is critical in the present invention that the ratio of aluminum to anion not exceed the stated ratio since excess aluminum will cause a polymeric shift so that a greater proportion of Band I aluminum compound is obtained and a lesser amount of the Band III aluminum is present.

Surprisingly, the present process does not require an aging step to obtain the high concentration of the Band III aluminum compound in the process. Even more surprising is that only the Band III aluminum can be prepared to the exclusion of the other bands.

The acids utilized in the process are sulfuric acid, nitrous acid, hydrofluoric acid, hydroiodic acid and hydrochloric acid.

The metallic aluminum used in the process may be in the form of powder, flakes, chips, etc., and is not restricted to any particular form. Obviously, the aluminum powder causes the reaction to proceed more rapidly because of the surface area involved.

The basic aluminum compounds of the invention may be obtained in solid form by any of the conventional methods of drying. For example, the drying process includes spray drying, drying under atmospheric temperature and pressure, rapid vacuum drying under atmospheric conditions, freeze drying and azeotropic distillation in an alcoholic solution. Of the drying processes, spray drying is the most preferable from the standpoint of economic cost and quality of the final product. The resulting powder may then be milled, micronized and classified to proper particle size depending on the composition to be prepared.

The basic aluminum compounds of the invention may be used as antiperspirants in the various forms well known in the art, for example, lotions, creams, roll-ons, pads, solid sticks and aerosols.

The basic aluminum compounds of this invention are especially useful in anhydrous suspension type systems well known in the art, such as roll-ons, solid sticks, pump and aerosol sprays, in which the powders are suspended in hydrophobic vehicles, for example fatty acid esters such as isopropyl myristate (WICKENOL®101), dibutyl phthalate, diisopropyl adipate (WICKENOL®116), dioctyl adipate (WICKENOL®158), volatile cyclic silicones, and the like. Advantageously, dioctyl adipate (WICKENOL®158) may be used in lieu of the cyclic silicones. WICKENOL®101, WICKENOL®116 and WICKENOL®158 are trademarks of Wickhen Products, Inc., Huguenot, N.Y.

The antiperspirant composition in the form of a lotion may contain suitable thickening agents such as magnesium aluminum silicates or have thickening effected by emulsifying a cosmetic oil or the like.

The composition in the form of a powder aerosol comprises a suspension of from about 1% to about 20% by weight of the basic aluminum compound in powder form; from about 0.1% to about 5% by weight of a suspending agent; from about 1% to about 25% by weight of a carrier liquid; and from about 50% to about 95% by weight of a propellant.

Various carrier liquids which may be utilized are disclosed in U.S. Pat. Nos. 3,968,203, 3,949,066 and 3,949,270, which patents are herewith incorporated by reference.

The propellant can be nitrogen, carbon dioxide, liquified hydrocarbon, halogenated hydrocarbon or mixtures thereof. Examples of suitable hydrocarbon propellants include trichlorofluoromethane, dichlorodifluoromethane, propane, butane, isopentane, isobutane, and the like.

The aerosol spray composition may also include suspending agents and thickening or gelling agents such as hydrophobic clays and colloidal silicas.

Accordingly, it is an object of the present invention to provide a process for preparing an enhanced antiperspirant active polymeric basic aluminum compound in high yields.

It is a further object of the present invention to provide a process for providing a high yield of a basic aluminum compound that is characterized by having a Band III percent aluminum value of at least 40 percent and a Band I percent aluminum compound not greater than 5 percent.

It is another object of the invention to provide a process which yields only Band III aluminum compounds.

It is still further object of the invention to prepare the enhanced active polymeric basic aluminum halides from acidic aluminum halide without a separate elevated temperature aging step in the process.

It is a yet still further object of the invention to provide an antiperspirant composition having a greater amount of the lower molecular weight enhanced antiperspirant active aluminum compounds by a more efficient process.

It is another object of the invention to increase the percentage of enhanced active aluminum chlorohydrate in an aerosol composition without the necessity of additional process steps or separation procedures.

It is an additional object of the invention to provide processes for preparing an increased percentage of the enhanced active aluminum chlorohydrate species in a single reaction vessel from aluminum chloride or aluminum and inorganic mineral acid without an additional separation or aging step.

In order to more fully and clearly illustrate the present invention, the following specific examples are presented. It is intended that the examples be considered as illustrative rather than limiting the invention disclosed and claimed herein. In the examples, all parts and percentages are on a weight basis unless otherwise specified.

EXAMPLE 1

A 50 gallon tank equipped for external heating was charged with 32 gallons of deionized water and 8.70 lbs. (3977gm) of aluminum metal. To the tank 26.8 lbs. of standard aluminum chloride hexahydrate solution is slowly added with stirring. After the initial exothermic reaction the batch was maintained at a temperature between 90° C. and 110° C. until a ratio of aluminum to chloride was 0.9–2.05:1. The liquor was immediately drawn off, filtered and spray dried in a co-current spray drier using inlet and outlet temperatures of 690° F. and 240° F. respectively. The resulting powder had an Al/Cl molar ratio of 1.95 and consisted of 56.9% Band III aluminum compound and 0% Band I aluminum compound.

The resultant powder may then be milled, micronized and classified.

In lieu of aluminum chloride there may be utilized any one of aluminum iodide, aluminum sulfate, aluminum fluoride, aluminum bromide and aluminum nitrite to obtain the corresponding basic aluminum compound.

EXAMPLE 2

Into a flask containing 100ml of deionized water and 100ml of 1 N hydrochloric acid is slowly added 5.4g of aluminum powder. The mixture is then heated and stirred at 90° C. until all of the aluminum is dissolved. Then additional aluminum is added until a ratio of aluminum to chlorine in the solution reaches 0.9–2.05:1. The mixture is cooled and filtered. The liquor was freeze-dried to obtain a white powder of hydrated basic aluminum chlorohydrate consisting entirely of Band III aluminum compound.

EXAMPLE 3

An aerosol composition is prepared having the following ingredients:

| Ingredient | % |
| --- | --- |
| Basic Aluminum Chlorohydrate from Example 1 | 15.0 |
| Isopropyl myristate (WICKENOL 101) | 6.0 |
| Silica (Aerosil 200) | 0.5 |
| Perfume | 0.2 |
| Propellant* | to 100 |

*50:50 by weight of trichlorofluoromethane and dichlorodifluoromethane

EXAMPLE 4

An aerosol composition is prepared having the following ingredients:

| Ingredient | % |
| --- | --- |
| Basic Aluminum chlorhydrate from Example 1 | 10.0 |
| Isopropyl myristate | 13.4 |
| Bentone 38 | 0.8 |
| Alcohol SDA-40 | 0.8 |
| Propellant* | to 100 |

*80% Isobutane/20% propane

EXAMPLE 5

An antiperspirant stick suspension is prepared as follows:

| Ingredient | % by wt. |
| --- | --- |
| Phase A | |
| Stearyl alcohol | 26.00 |
| 2-Ethylhexyl palmitate (WICKENOL ® 155) | 14.50 |
| Di(2-ethylhexyl) adipate (WICKENOL ® 158) | 14.25 |
| Phase B | |
| Volatile silicone | 20.00 |
| Phase C | |
| aluminum chlorohydrate from Example 1(WICKENOL ® CPS) | 20.00 |
| Phase D | |
| Arachidyl Propionate/Polymer powder (POLYTRAP ® 801) | 5.00 |
| Wheat germ glycerides (WICKENOL ® 535 VITA-COS) | 0.25 |
| Fragrance | QS |

The ingredients of Phase A are mixed and heated to 65° C. to liquify the stearyl alcohol. The silicone is then added to the mixture under low speed agitation while maintaining the temperature at 65° C. The aluminum chlorohydrate is slowly added and the heating is stopped. At about 62° C. the arachidyl propionate/polymer powder and the wheat germ glycerides are added. The mixture is stirred and the fragrance is added. The mixture is then poured into molds at about 58° C. The composition has a melting point of 50°–55° C.

EXAMPLE 6

A water-in-oil emulsion antiperspirant roll-on composition is prepared as follows:

| Ingredient | % by wt. |
| --- | --- |
| Suspension agent (Q2-3225(Dow Corning)) | 6.00 |
| Volatile cyclic silicone fluid | 13.50 |
| Di(2-ethylhexyl) adipate (WICKENOL ® 158) | 13.50 |
| Wheat germ glycerides (WICKENOL ® 535 VITA-COS) | 0.25 |
| Basic aluminum chlorohydrate | |

| Ingredient | % by wt. |
| --- | --- |
| from Example 1 | 28.00 |
| Demineralized water | 37.75 |

Silicone fluid, di(2-ethylhexyl) adipate and wheat germ glycerides are mixed until a uniform blend is obtained. The basic aluminum chlorohydrate, suspension agent and water are slowly added to the blend and the mixture is stirred under high speed. Mixing is continued for 15 minutes and the mixture is poured into containers.

EXAMPLE 7

A dry roll-on suspension type antiperspirant composition is prepared as follows:

| Ingredient | % by wt. |
| --- | --- |
| Phase A | |
| Volatile cyclic silicone fluid | 40.00 |
| Blended porosity ester (WICKENOL ® 161) | 5.00 |
| Bentone powder | 2.00 |
| Ethanol SDA40 | 2.00 |
| Phase B | |
| Volatile cyclic silicone fluid | 25.00 |
| Blended porosity ester (WICKENOL ® 161) | 5.00 |
| Phase C | |
| aluminum chlorohydrate from Example 1 (WICKENOL ® CPS) | 20.00 |
| Phase D | |
| Demineralized water | 1.00 |

The silicone fluid and the ester of Phase A are mixed together. The mixture is then mixed under high speed in an Eppenbach Homomixer and the bentone powder is slowly added followed by addition of the ethanol.

Separately, the ingredients of Phase B are blended until clear. The blend is then mixed under high speed and the aluminum chlorohydrate is added. The mixture is added to the Phase A ingredients and mixed under high speed for five (5) minutes. The mixture is then moderately stirred and the demineralized water is added.

What is claimed is:

1. An improved process for preparing an enhanced antiperspirant active aluminum compound having the empirical formula:

$$Al_2(OH)_{6-a}X_a \tag{I}$$

wherein X is Cl, Br, F, I, SO$_4$ and NO$_2$, a is about 1.0 to about 4.0, which is further characterized by (a) a Size Exclusion Chromatograph Test Band corresponding to Band III of the Standard Basic Aluminum Chloride Solution Size Exclusion Chromatograph, and (b) a Band III percent aluminum value of at least 40 percent, which comprises reacting an aluminum compound of the formula: Al$_n$X$_m$, wherein X is an hereinbefore described, n is 1 or 2, and m is 1 or 3, with aluminum metal in an aqueous medium at a temperature between 50° C. and 195° C. until a ratio of aluminum to anion of 0.50–2.5:1 is obtained, and then recovering the resultant product without elevated temperature aging.

2. The process of claim 1 wherein the amount of Band III aluminum value of the resultant product is at least 90 percent.

3. The process of claim 1 wherein the Band I percent aluminum value of the resultant product is not greater than about 5 percent.

4. The process of claim 1 wherein the ratio of aluminum to anion of the resultant product is 0.90–2.05:1.

5. The process of claim 1 wherein the reaction temperature is about 90° to 120° C.

6. The process of claim 1 wherein the compound of formula Al$_n$X$_m$ is prepared in situ.

7. The process of claim 1 including filtering and then spray drying the resultant product.

8. The process of claim 1 wherein X is Cl.

9. A basic aluminum compound having the formula:

$$Al_2(OH)_{6-a}X_a$$

wherein X and a are as hereinbefore described, which is prepared according to the process of claim 1.

10. The basic aluminum compound of claim 9 which is a basic aluminum chloride.

* * * * *